US010019555B2

(12) United States Patent
Manice et al.

(10) Patent No.: US 10,019,555 B2
(45) Date of Patent: Jul. 10, 2018

(54) INTERACTIVE RESPIRATORY DEVICE USAGE TRACKING SYSTEM

(71) Applicant: Cohero Health, Inc., New York, NY (US)

(72) Inventors: Melissa P. Manice, New York, NY (US); Charles D. Manice, New York, NY (US); Daniel W. Weinstein, New York, NY (US)

(73) Assignee: Cohero Health, Inc., New York, NY (US)

( * ) Notice: Subject to any disclaimer, the term of this patent is extended or adjusted under 35 U.S.C. 154(b) by 660 days.

(21) Appl. No.: 14/518,529

(22) Filed: Oct. 20, 2014

(65) Prior Publication Data
US 2015/0112707 A1   Apr. 23, 2015

Related U.S. Application Data

(60) Provisional application No. 61/893,210, filed on Oct. 19, 2013, provisional application No. 62/055,801, filed on Sep. 26, 2014.

(51) Int. Cl.
G06Q 50/00     (2012.01)
G06F 19/00     (2018.01)
(Continued)

(52) U.S. Cl.
CPC ....... *G06F 19/3462* (2013.01); *A61M 15/008* (2014.02); *A61M 15/0083* (2014.02);
(Continued)

(58) Field of Classification Search
CPC ..... G06Q 50/22–50/24; G06F 19/322–19/327; G16H 20/13
See application file for complete search history.

(56) References Cited

U.S. PATENT DOCUMENTS 5,333,106 A   7/1994   Lanpher et al.
5,363,842 A   11/1994  Mishelevich
(Continued)

FOREIGN PATENT DOCUMENTS

DE   102014204939   12/2014
EP   0 387 222 A1    9/1990
(Continued)

OTHER PUBLICATIONS

Smanis I., Poursanidis G., Angelidis P., Tzallas A.T., Tsalikakis D. (2013) Managing Children's Asthma with a Low Cost Web-Enabled Multifunctional Device. In: Angelis C.T., Fotiadis D., Tzallas A.T. (eds) Ambient Media and Systems. AMBI-SYS 2013. Lecture Notes of the Institute for Computer Sciences, Social Informatics and Telecommunications Engineering, vol. 118. Springer, Cham.

*Primary Examiner* — Sheetal R Paulson
(74) *Attorney, Agent, or Firm* — Thomas A. Runk; Brooks Kushman P.C.

(57) ABSTRACT

A monitoring system for inhalers includes a tracker module configured to be secured to a variety of inhalers, including both controller and rescue inhalers. The tracker module has a flexible shell that fastens around an inhaler and an activation sensor for sensing use of the inhaler, an internal memory for storing inhaler use data, and a communication component for forwarding the stored usage data to a processor for analyzing the data. The activation sensor is flexibly connected to the flexible shell with a flexible cable and is placed over the end of the inhaler canister. The processor is located in a local station separate from the tracker module but wirelessly synchronized therewith. In one embodiment, the system also collects lung function data, e.g., from a spirometer, and then processes all of the controller inhaler data, the rescue inhaler data, and the lung function data, to generate alerts and other messages.

27 Claims, 12 Drawing Sheets

(51) Int. Cl.
*G16H 20/13* (2018.01)
*A61M 15/00* (2006.01)
*G09B 19/00* (2006.01)
*A61B 5/087* (2006.01)
*G06Q 50/22* (2018.01)
*G06Q 10/08* (2012.01)

(52) U.S. Cl.
CPC ............ *G09B 19/00* (2013.01); *G16H 20/13* (2018.01); *A61B 5/087* (2013.01); *A61M 15/009* (2013.01); *A61M 15/0051* (2014.02); *A61M 2205/18* (2013.01); *A61M 2205/332* (2013.01); *A61M 2205/3334* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/505* (2013.01); *A61M 2205/52* (2013.01); *A61M 2205/581* (2013.01); *A61M 2205/582* (2013.01); *A61M 2205/60* (2013.01); *A61M 2205/8212* (2013.01); *A61M 2230/40* (2013.01); *G06Q 10/087* (2013.01); *G06Q 50/22* (2013.01)

(56) References Cited

U.S. PATENT DOCUMENTS

| | | |
|---|---|---|
| 5,536,249 A | 7/1996 | Castellano et al. |
| 5,556,421 A | 9/1996 | Prutchi et al. |
| 5,622,163 A | 4/1997 | Jewett et al. |
| 5,676,129 A | 10/1997 | Rocci, Jr. et al. |
| 6,085,742 A | 7/2000 | Wachter et al. |
| 6,138,669 A | 10/2000 | Rocci, Jr. et al. |
| 6,165,155 A | 12/2000 | Jacobsen et al. |
| 6,190,326 B1 | 2/2001 | McKinnon et al. |
| 6,192,876 B1 | 2/2001 | Denyer et al. |
| 6,202,642 B1 | 3/2001 | McKinnon et al. |
| 6,615,825 B2 | 9/2003 | Stenzler |
| 6,945,954 B2 | 9/2005 | Hochman et al. |
| 6,958,691 B1 | 10/2005 | Anderson et al. |
| 6,990,975 B1 | 1/2006 | Jones et al. |
| 7,198,172 B2 | 4/2007 | Harvey et al. |
| 7,233,228 B2 | 6/2007 | Lintell |
| 7,424,888 B2 | 9/2008 | Harvey et al. |
| 7,454,267 B2 | 11/2008 | Bonney et al. |
| 7,481,772 B2 | 1/2009 | Banet |
| 7,599,737 B2 | 10/2009 | Yomtov et al. |
| 7,658,122 B2 | 2/2010 | Farina et al. |
| 7,658,737 B2 | 2/2010 | Hartlaub et al. |
| 7,747,345 B2 | 6/2010 | Ohmura et al. |
| 7,813,880 B2 | 10/2010 | Vaidya et al. |
| 7,833,213 B2 | 11/2010 | Katz et al. |
| 8,061,353 B2 | 11/2011 | Easley et al. |
| 8,095,197 B2 | 1/2012 | Santini, Jr. et al. |
| 8,342,172 B2 | 1/2013 | Levy et al. |
| 8,403,907 B2 | 3/2013 | Sheppard, Jr. et al. |
| 8,485,979 B2 | 7/2013 | Giftakis et al. |
| 8,551,039 B2 | 10/2013 | Veit et al. |
| 8,556,867 B2 | 10/2013 | Krulevitch et al. |
| 8,565,883 B2 | 10/2013 | Lozano |
| 8,612,006 B2 | 12/2013 | Lozano et al. |
| 8,702,683 B2 | 4/2014 | Baym et al. |
| 2002/0151770 A1 | 10/2002 | Noll, III et al. |
| 2003/0205229 A1 | 11/2003 | Crockford et al. |
| 2004/0039295 A1 | 2/2004 | Olbrich et al. |
| 2004/0172303 A1 | 9/2004 | Declerck et al. |
| 2005/0172958 A1 | 8/2005 | Singer et al. |
| 2006/0130838 A1 | 6/2006 | Lee et al. |
| 2007/0016443 A1* | 1/2007 | Wachman ............... G06Q 50/22 705/2 |
| 2009/0194104 A1 | 8/2009 | Van Sickle |
| 2010/0145303 A1 | 6/2010 | Yodfat et al. |
| 2010/0163041 A1 | 7/2010 | Hyde et al. |
| 2010/0192948 A1 | 8/2010 | Sutherland et al. |
| 2010/0241501 A1* | 9/2010 | Marshall ................ G06Q 30/00 705/14.13 |
| 2010/0282245 A1 | 11/2010 | Star et al. |
| 2011/0225008 A1 | 9/2011 | Elkouh et al. |
| 2011/0226237 A1 | 9/2011 | Morrison |
| 2011/0247623 A1* | 10/2011 | McCarthy ............. A61M 16/06 128/205.11 |
| 2011/0253139 A1 | 10/2011 | Guthrie et al. |
| 2012/0247235 A1 | 10/2012 | Adamo et al. |
| 2013/0008436 A1 | 1/2013 | Von Hollen et al. |
| 2013/0186392 A1 | 7/2013 | Haartsen et al. |
| 2013/0206142 A1* | 8/2013 | Dudley ............. A61M 15/0066 128/203.15 |
| 2015/0174348 A1* | 6/2015 | Tunnell ............. A61M 16/0051 128/200.14 |
| 2017/0065777 A1 | 3/2017 | Koerner |

FOREIGN PATENT DOCUMENTS

| | | |
|---|---|---|
| EP | 1220802 B1 | 2/2004 |
| EP | 1 670 533 A1 | 6/2006 |
| EP | 1135056 B1 | 8/2006 |
| EP | 1223855 B1 | 8/2006 |
| EP | 1 330 283 B1 | 9/2006 |
| EP | 1499275 B1 | 11/2010 |
| EP | 2414013 | 2/2012 |
| EP | 1499376 B1 | 8/2016 |
| WO | 93/12823 A2 | 7/1993 |
| WO | 00/16836 A1 | 3/2000 |
| WO | 03092575 A2 | 11/2003 |
| WO | 03092576 A2 | 11/2003 |
| WO | 03092773 A1 | 11/2003 |
| WO | 2005/028008 A1 | 3/2005 |
| WO | 2008115906 A1 | 9/2008 |
| WO | 2009/022139 A1 | 2/2009 |
| WO | 2010112878 A1 | 10/2010 |
| WO | 2013/061240 A1 | 5/2013 |
| WO | 2014/004437 A1 | 1/2014 |
| WO | 2014/033229 A1 | 3/2014 |
| WO | 2014049086 A1 | 4/2014 |
| WO | 2015178907 A1 | 11/2015 |
| WO | 2016048435 A1 | 3/2016 |

* cited by examiner

INTERACTIVE RESPIRATORY DEVICE USAGE TRACKING SYSTEM

CROSS REFERENCE TO RELATED APPLICATIONS

This application claims benefit of U.S. Provisional Application Nos. 61/893,210 filed Oct. 19, 2013, and 62/055,801 filed Sep. 26, 2014, the disclosures of which are incorporated by reference herein.

BACKGROUND OF THE INVENTION

Field of the Invention

The present invention generally relates to the use of respiratory devices, such as inhalers and spirometers, and more particularly to a system and method of encouraging compliance with a usage plan and for monitoring and tracking that compliance.

Description of the Related Art

Inhalers are commonly used to provide oral or intra-nasal medication to patients. They can be used for relief on an as-needed basis, as well as for application of a prescribed course of treatment. The user segment of particular significance to the present invention is the large population for whom there is a prescribed course of treatment using an inhaler. The effectiveness of the treatment regimen is dependent on compliance with the treatment regimen, and this has traditionally been a problem area. There are approximately 26 million persons in the United States alone who suffer from chronic asthma, and whose poor adherence rate greatly contributes to an estimated $300 billion in preventable indirect and direct medical costs annually. On average, children and adults adhere to their prescription schedule with less than 50% success rate (i.e., they skip their medication more than 50% of the time). One easily quantifiable direct cost of poor adherence is the $18 billion spent on Emergency Room (ER) visits where poor inhaler medication adherence is cited as the number one cause for ER visits.

A higher degree of compliance would improve results in many cases, and in those cases where the treatment is ineffective the physician and patient can move on to a different solution rather than continuing with a course of treatment thinking that it would be effective if followed.

The medical field has long recognized the problem of a patient visiting a physician and having very imprecise recollection of how often the inhaler has been used. Solutions proposed include those described in U.S. Pat. No. 6,958,691 to Anderson, et al, U.S. Patent No. 6,202,642 to McKinnon, U.S. Patent No. 5,363,842 to Mishelevich, Published U.S. Patent Application No. 2011/0253139 of Guthrie, et al, Published U.S. Patent Application No. 2009/0194104 of Van Sickle, and published international application WO 2014/004437 of Engelhard, et al. These prior solutions monitor usage and track adherence, but are often bulky, or require customized inhalers (i.e., cannot be easily fitted to and operated with any inhaler already in use). Some also require special purpose hardware to collect data and forward it to the physician. And all are inadequate as to providing encouragement and incentives for adherence.

An additional problem, exacerbated by failure to use an inhaler as prescribed, but a separate problem nonetheless, is the difficulty in obtaining sufficient data regarding changes in lung function, and in making timely adjustments of a prescribed treatment regimen in accordance with updated lung function.

SUMMARY OF THE INVENTION

There is a need, then for a system and method that (a) can be used with the majority of inhaler devices already in use and is likely compatible with those developed in the future, (b) is simple in both design and operation, thereby encouraging more widespread use, and (c) provides positive encouragement/motivation for compliance.

There is a further need for a system whereby real-time lung function data can be obtained, correlated with actual inhaler usage, and the patient treatment regiment reassessed and the patient advised of the updated treatment regimen without having to visit a physician.

There is a still further need for a system that can make use of respiratory data in real time and use predictive modeling, on a specific patient's data and optionally data across a larger patient population, to alert the patient of potential adverse events in advance.

There is a still further need for a system that can make use of respiratory data of a larger number of people to conduct population-level analysis. For example identifying sub-populations that respond similarly to medications.

According to the present invention, a compact tracking module made of a flexible material (e.g., silicone) can be wrapped around a conventional inhaler or otherwise easily secured to an inhaler. The tracking module includes a sensor for sensing operation of the inhaler, internal memory for storing a record (e.g., a time/date stamp) of that dose, and a wireless communication component for forwarding the stored data, eventually to a remote server from which the data can be accessed by a physician. In one embodiment, this module fits over standard L-shaped medication inhalers of different sizes and some other shapes, e.g., cylindrical. In another embodiment, this module fits over disk shaped medication inhalers.

In a preferred embodiment, the invention further includes an application that not only monitors/tracks the inhaler usage but also interacts with the patient to encourage compliance. The application can send messages to the patient or otherwise display incentives in the form of messages, rewards, status levels, points, etc., all of these possibly in the context of a game and/or real world incentives such as gifts or points which can be redeemed for medication discounts, consumer goods, etc. In a still further embodiment, the invention collects additional data for analysis, and enables predictive modeling for possible alerts to the patient and/or physician. By way of example, the tracking module can be alternately secured to either a controller inhaler or a rescue inhaler of an individual, and the system can also collect lung function data (e.g., from a spirometer), and can use data analytics and predictive modeling to collect and analyze trends across patient populations, and generate alerts or other messages to the patient, physician, caregiver, family member, insurance carrier, or other third party. In a still further embodiment, the invention encourages compliance to spirometer use.

The interactive tracking application can be run on a server with the patient device(s) simply forwarding the data to the server and interacting directly with the server, but it may be preferred that the tracking module is paired with a local device, e.g., a smartphone or other portable electronic device to transmit the data to the local device using low power short range communication. The interactive tracking application is run on the smartphone to provide some analysis of the data and feedback to the user, but also other functions related to inhaler use, e.g., tracking and reminding of doctor's appointments, tracking and informing of the number of doses remaining in the inhaler and facilitating refill, making of emergency phone calls, storing treatment plan, displaying educational information and awarding of prizes as incentives for compliance.

The tracking module will exhibit very low power consumption due to the combined effects of low energy communications (e.g., Bluetooth or Near Field Communication) and an operational design as a largely passive device that spends the majority of its time in an off/standby mode to conserve battery life. The device is ordinarily in an off/standby mode, and automatically awakens to store a date/time stamp when inhaler is used. The device will thereafter attempt to connect and transfer the data, but if unsuccessful will continue trying at regular intervals (e.g., once an hour) until successful.

A further advantage is that, with the tracking module having its own internal memory, the inhaler and smartphone need not be in proximity when dose is taken.

A "Sync" button permits pairing and data-transmission without taking dose, so optionally the periodic retry for data transmission can be dispensed with until manual syncing at an appropriate later time. The internal memory is preferably large enough to hold a number of dose records, making occasional syncing possible without losing data.

According to the present invention, one respiratory device that can be used in the system is a spirometer, which is used to assess lung function. By tracking these lung function measurements over time, trends can be identified. Response to different inhaler treatment regimens could be seen, deterioration of lung function suggesting imminent respiratory event could be spotted, and predictive modeling could be used with all available data to predict potential future events/issues more reliably and provide appropriate messages to the patient and/or healthcare support to prevent such events.

BRIEF DESCRIPTIONS OF THE DRAWINGS

The invention will be more clearly understood from the following detailed description in conjunction with the accompanying drawings, wherein.

DETAILED DESCRIPTION OF THE INVENTION

Figure 1:
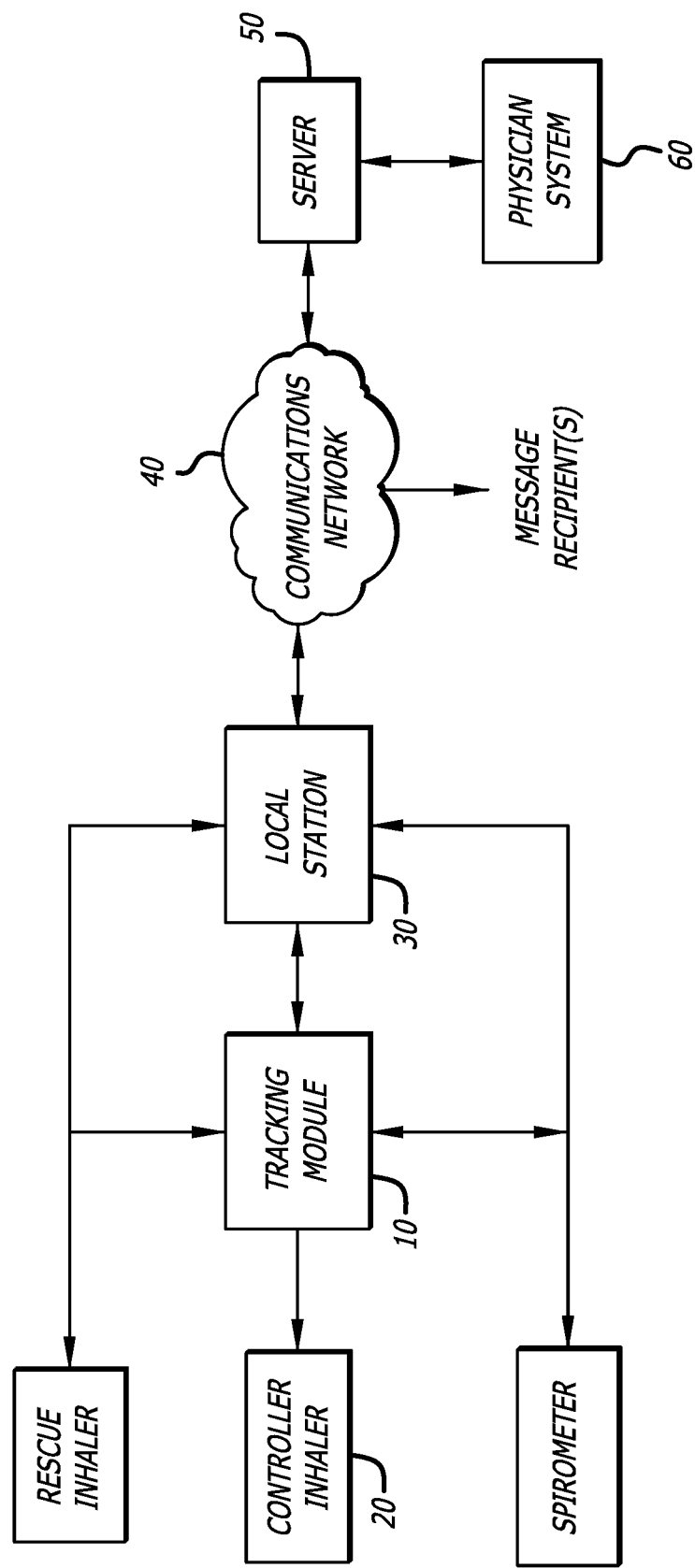
FIG. 1 is a block diagram of an adherence tracking system according to a preferred embodiment of the present invention.

The system of the invention is very broadly illustrated in FIG. 1. A tracking module 10 monitors operation of an inhaler 20 and reports to a local station 30 with processing and communication capabilities. In the description which follows, the station 30 will be assumed to be a smartphone, although this is by way of example only. The station 30 may alternatively be a tablet, personal computer, or some other device carried by the user. In a less preferred but viable implementation the station 30 may be a desktop computer or other fixed processing system. The local station 30 processes the received signals for transmission via a wired or wireless network 40 to a server 50. The local station 30 may additionally process the data and provide analysis results or reports to the user, but in the preferred embodiment of the invention it is contemplated that the primary data processing location is at the server 50. Analysis results can then be accessed by a healthcare professional (e.g., a physician, nurse, or healthcare researcher) or other third party from a remote terminal 60. The healthcare professional can make use not only of a specific patient's data but also respiratory data of a larger number of people to conduct population-level analysis. This may allow identification of sub-populations that respond similarly to medications, e.g., identifying trends not known before, such as children aged 10-15 responding much better to medicine A than medicine B.

According to an embodiment of the invention, a monitoring server, most likely the server 50, forwards specific medical information to the Electronic Medical Records system of the physician, including lung function and medication adherence, and can also receive patient information from the EMR, for inclusion in its analysis and/or communicating to the patient. As one example, the server can access the EMR to obtain the patient's prescription information and use that in sending reminders to the patient and in assessing patient compliance.

The system of the invention can also optionally accept usage data from both controller and rescue inhalers as well as lung function data from a spirometer, as schematically shown in FIG. 1. Each of the three respiratory devices can incorporate its own sensing, data storage and/or communications interface as needed to supply data to the local station, although in a preferred embodiment the inhalers each use a tracking module 10. The data from each of the three can be gathered and forwarded to the local station 30 by its own respective module, or all data collected in a shared tracking module 10, or a combination of shared and dedicated modules.

It is also possible within the scope of the present invention for the system to be designed and operated to monitor only lung function data via a spirometer, and to interact with the patient to encourage proper and timely use of the spirometer to provide needed data and to facilitate anticipation of potential adverse respiratory events.

Figure 2:
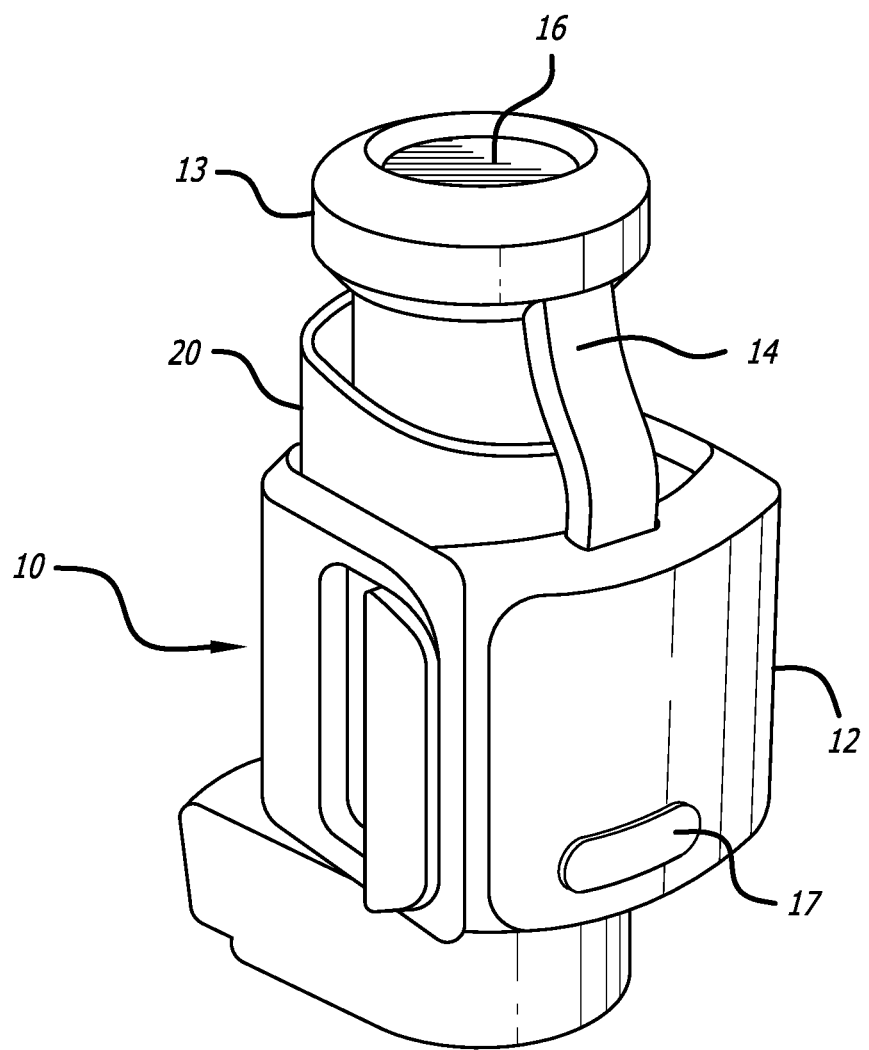
FIG. 2 is a perspective view of one example of a tracking module according to the present invention.
Figures 3A, 3B, 3C:
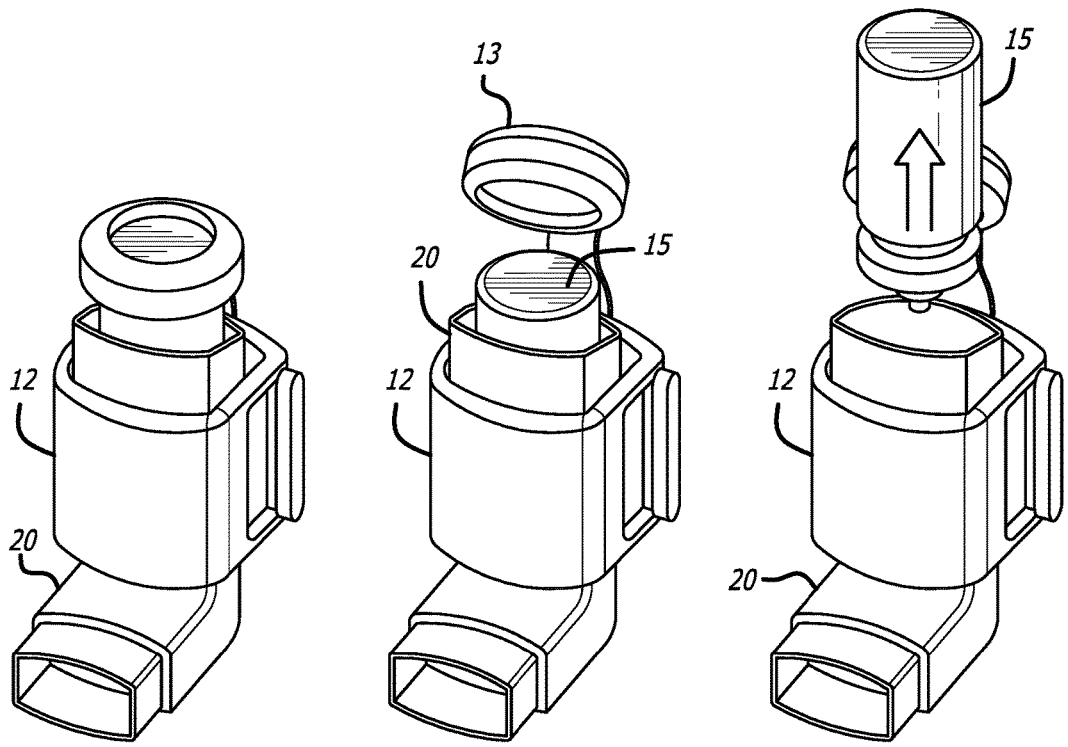
FIGS. 3A-3C are perspective views of the tracking module of FIG. 2, for showing the process of removing and replacing the medication canister.
Figure 5:
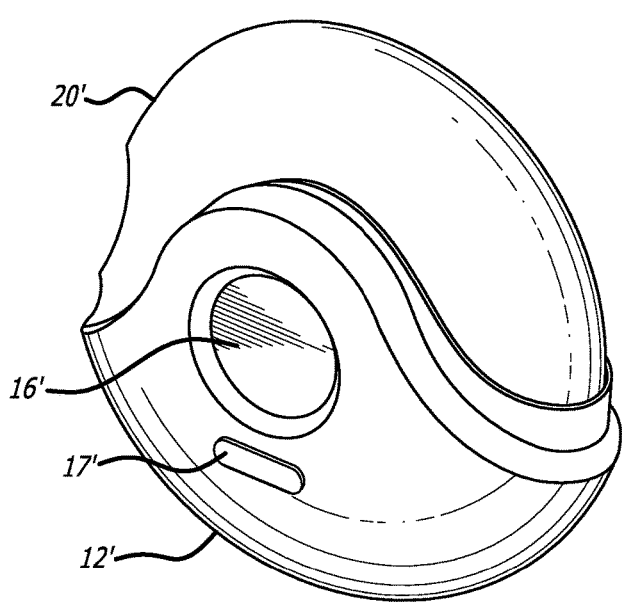
FIG. 5 is a perspective view of a tracking module according to a second embodiment of the invention.
Figure 4A:
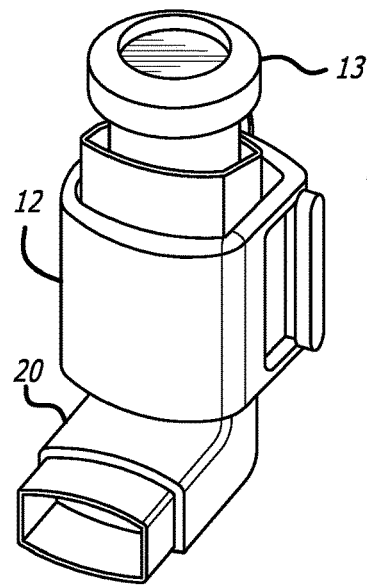
FIGS. 4A-4C show the tracking module of FIG. 2 mounted to the inhaler (FIG. 4A) and showing front (FIG. 4B) and rear (FIG. 4C) views of the tracking module before mounting to the inhaler.
Figure 4B:
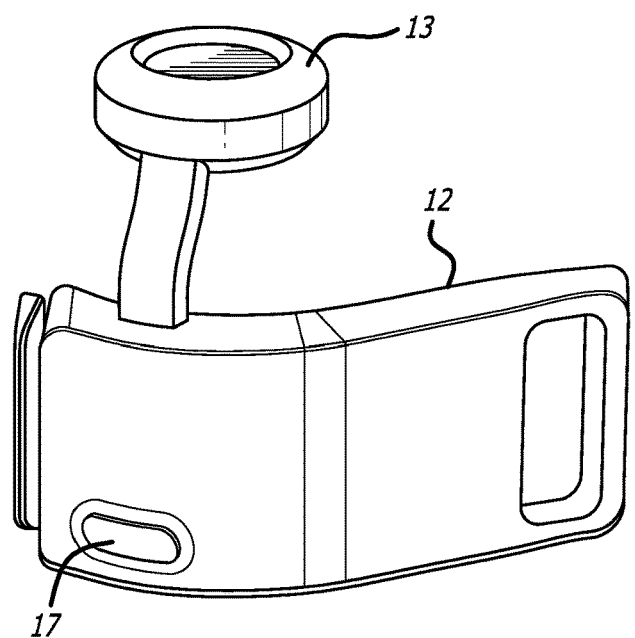
Figure 4C:
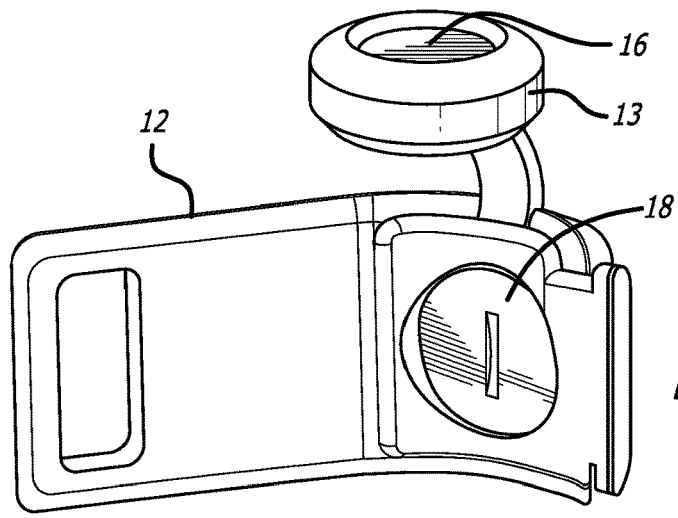
Figure 6A:
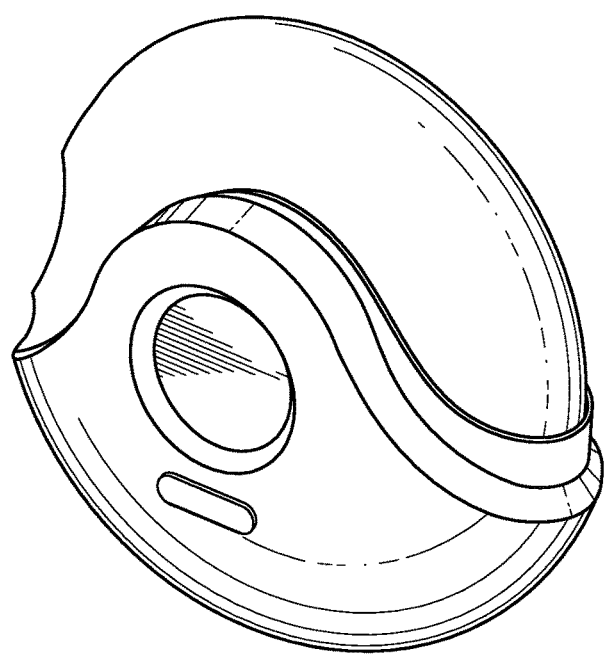
FIGS. 6A-6C show the tracking module of FIG. 5 mounted to an inhaler (FIG. 6A), end (FIG. 6B) and perspective (FIG. 6C) views of the tracking module separate from the inhaler.
Figure 6B:
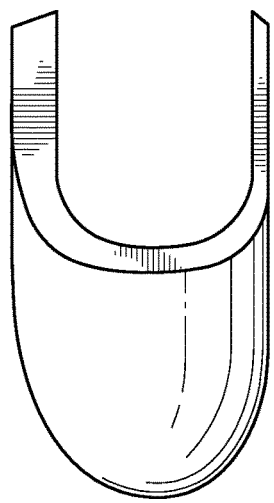
Figure 6C:
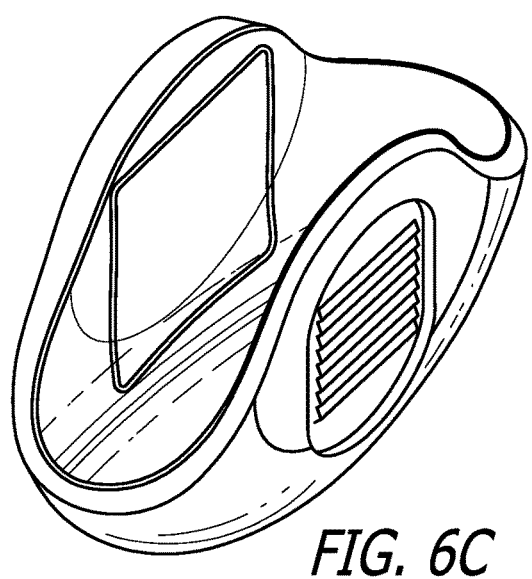

An example of a tracking module 10 according to the invention is illustrated in FIGS. 2-4, with the tracking module in this example comprising a shell 12, made of silicone or other flexible material, which can wrap around a standard inhaler 20 and interlock its ends with one another to be held in place. Alternatively or in addition, it may be secured to the inhaler by means of a snap, magnet, moldable metal wire, Velcro, etc. Alternatively it may be secured over a device without any attachment device, using elasticity to make it cling to the inhaler. The shell 12 is shown as having a cap 13 attached to the shell by a flexible cable 14. As shown in FIG. 2, the cap 13 can attach to the end of a medicament canister 15 after the canister is inserted into the body of inhaler 20. FIGS. 3A-3C illustrate the process of removing the cap 13 and removing and replacing the canister 15.

In a preferred embodiment of the invention, the tracking module includes:
- a Bluetooth low energy device, e.g., a TI CC2541 Bluetooth 4.0 LE IC;
- a short-term memory device, e.g., the TI CC2541 IC's internal RAM for holding 30 records of 20 bytes each, requiring a total of 600 bytes;
- a pressure activated sensor 16 (in the form of a mechanical switch, an electro-mechanical switch, a piezo-electric switch, or some other pressure-sensitive activator or pressure sensitive switch) that is activated when the user depresses the inhaler to take a dose of medication;
- a battery, e.g., a CR2032 220 mAH button cell battery (not shown), located under a battery cover 18;
- a PCB Board with a Bluetooth 4.0 LE Module and with two accessing buttons (one for Press-Count, another for Sync);
- an external "sync" button 17; and
- firmware, e.g., based on Bluetooth 4.0 LE communication protocol, enabling Press-Count & Sync button functionalities discussed below.

In operation, each tracking module has a unique identification number and is "paired"/"synced"/"married" to a unique user smartphone such that each tracking module has a direct feedback loop with a single user smartphone (hereafter referred to as "pairing"). The pairing is performed once, either automatically or using the "sync" button 17 (also referred to as an "on/off & pairing switch") on the exterior of the tracking module, e.g., the user may open the app on the smartphone, tell the phone to find a device, and the app will find the device if the user presses either the sync button or puffs when the app is looking to sync with a device. The same tracker can be re-paired with different smartphones.

The tracking module records a date-stamp each time the pressure activated sensor 16 is depressed (the "DateStamp.") The switch 16 could be provided anywhere on or connected to the tracking module, and not tied to actual medication dispensing, for the user to press after taking a dose of medication. In a preferred embodiment, the switch 16 mounts to the top of the medication canister so that the switch is activated each time that the canister is depressed. Alternatively, the operation of the inhaler to deliver a dose could be detected when the user activates any other mechanical mechanism for dispensing medication. The DateStamp is a record of the date and time of activation, preferably associated with a unique "Puff ID." Since the dosage per activation is fixed and known, no data need be recorded except the number of activations and the times at which they occurred. The DateStamp is stored in the internal memory of the tracking module. When a DateStamp is recorded, the tracking module immediately searches for the paired device. If the paired device is found, the tracking module transmits the DateStamp, the smartphone confirms receipt, and the tracking module returns to "inactive" or "sleep" mode. If proximity is not immediately found, the tracking module regularly seeks the paired smartphone, e.g., every 7-10 minutes, or for a thirty second window once per hour, or some other suitable interval. Once proximity is found, the tracking module transmits all stored DateStamp(s) and returns to "inactive" or "sleep" mode.

An alternative tracking module configuration is shown in FIGS. 5, 6A, 6B, and 6C, designed for use with a Diskus® inhaler 20'. In this case, the tracking module comprises a saddle-shaped shell 12' designed to fasten onto the Diskus over the exterior portion of the inhaler body that rotates. This alternative tracking module configuration will include the same electronic internal components, and will respond to its pressure sensitive switch 16' and sync button 17' (also known as the on/off & pairing switch) in the same manner as the HFA model of tracking module shown in FIGS. 2-4. In this embodiment, switch 16' is not mechanically tied to inhaler activation, but is a standalone button that can be activated by the user after each dose to indicate that a dose has been delivered. Of course, it would also be possible to have an activation-sensing switch in addition to or in place of the standalone switch.

There are a number of features and advantages that flow from the tracking module having the design and operating characteristics as described above. It will exhibit very low power consumption due to the combined effects of low energy Bluetooth communications and an operational design as a largely passive device that spends the majority of its time in an off/standby mode to conserve battery life. For example, the device is ordinarily in an off/standby mode, and when the button 16 is depressed, the tracking module wakes up from standby mode, and attempts to connect with a mobile device for brief period of time. If it succeeds, the stored data is immediately transferred and the module returns to its off/standby mode. If it is unsuccessful in immediately connecting to a paired mobile device, the tracking module places itself in an off/standby mode and wakes itself at intervals (e.g., once per hour) and for durations (thirty seconds) that will not result in significant power consumption.

A further advantage is that, with the tracking module having its own internal memory, the inhaler and smartphone need not be in proximity when a dose is taken.

In addition, the tracking module shell made of silicone and wrapping around the inhaler instead of mounting on top of the inhaler leads to an elastic and flexible package. Not only is this easier to use, but this structure also allows the module to fit on different size HFA inhalers as well as other shapes, including disk shaped inhalers, e.g., Advair Diskus.

Still further, conventional inhaler practice has been to use one inhaler for "controller" medication, inhaled daily no matter how a patient feels, to provide sustained patient improvement and prevent attacks and hospitalization, and a different inhaler for "rescue" medication, inhaled only when the patient is having difficulty breathing or an asthma attack. The tracking module according to the invention can be used for both controller and rescue medication inhalers.

The "Sync" button permits pairing and data-transmission without taking a dose, and the tactile feedback on pressing the switch informs the user that the switch has in fact been pushed, decreasing repeated and unnecessary activations.

Additional features that could be included as desired. By way of example:
- A vibrate function or audible function could be added to the tracking module (or to the smartphone application) whereby the tracking module and/or smartphone would vibrate or sound an alarm at regular intervals if a dose is not taken.
- A locate feature could be added to the tracker module whereby the user could cause the tracking module to make a sound in order for the user to locate the device (e.g., if the device is misplaced in a cabinet or fallen under a couch, etc.)

Light functions could be added to the tracking module, e.g., a low battery light, order refill indicator (i.e., when a few doses are left), or to indicate that it is time to take a dose.

A dose counter display could be added to the tracking module to display to the user the number of doses remaining.

Mechanisms based on other than pressure sensing could be used to detect activation of inhaler, e.g., by sensing movement of the canister or of drug exiting the inhaler.

Additional or alternative forms of wireless communication could be made available for communication between the tracking module and local station 30, e.g., Wifi, Mobile cell phone network; or other wireless communications; indeed it would be possible to do away entirely with the smartphone, having the tracking module able to communicate wirelessly with the network 40.

The tracking module could be provided with a flow measurement function so that the tracking system could track not only the number of doses administered but the amount of the medication inhaled, and could also or alternatively connect wirelessly to a wireless spirometer, so that the tracking system could monitor lung function to measure how medication use impacts a patient's ability to breath.

The local station 30 could be an in-home beacon. Such a beacon could be a WiFi enabled hardware device that plugs into a standard wall outlet and is in a permanent and constant receive mode state. The beacon could then sync to the tracking module either in response to user pressing the sync button, or the pairing could happen in response to detected activation of the inhaler The beacon could relay data from tracking module, via WiFi and the internet to a cloud-based tracking program application In addition to the tracking module, the system of the present invention includes a local station 30 which, in the preferred embodiment, is a smartphone running an application via which the smartphone will interface with the tracking module, and transmit data as appropriate to the server 50. More than simply storing and forwarding usage data, the application interacts with the user to facilitate usage tracking, and to encourage compliance. The smartphone thus forms a communications component for presenting to the patient incentives for compliance with a desired usage plan. The incentives can be communicated in the form of an app display presenting points earned, rewards earned or for which earned points can be redeemed, an adherence game score or status level, etc. Alternatively or in addition, the incentives can be presented to the patient in the form of text messages or other communications.

Another aspect of the invention is that it can adapt user messaging to user behavior, delivering more or fewer messages, dependent upon the consistency of user behavior, and dependent upon user preferences. The user can set his notification preferences, and notifications will turn off if he takes his medication (i.e., good user behavior vs. bad user behavior). Thus, rather than a one user fits all system, it can adapt to each user, his preference and his performance. An illustrative example would be, for a system recognizing a three hour time window during which the next scheduled inhaler use is to occur, the system may have messages that are triggered at different times, e.g., a reminder one hour in advance of the next scheduled time for inhaler use, at the time scheduled for inhaler use, once per hour during the three-hour window, and a "dose missed" message after that. It may send reminders at all of these events for a patient with a bad compliance record, and to the patient with a good compliance record may only send one reminder shortly before the end of the three-hour window. It is also possible to have the content of the messages differ for persons with good compliance vs. persons with bad compliance. The patient may, in a Settings menu, elect between more frequent and less frequent reminders, and the system can then take into account both the user preference and the compliance history in determining the frequency of the reminders, i.e., how many and which reminders are to be sent.

FIGS. 7-14 illustrate screens which may be presented to the user during operation of the system. In a preferred embodiment, the application employs an avatar "Hero" interface that communicates through automated (but intelligent) messaging responsive to particular user adherence and response rates. The application uses the smartphone clock to calculate most auto-messaging, or the messages can be generated at the cloud server and sent to the smartphone via text or push notification. The functions contained in each screen are described below.

Figure 7:
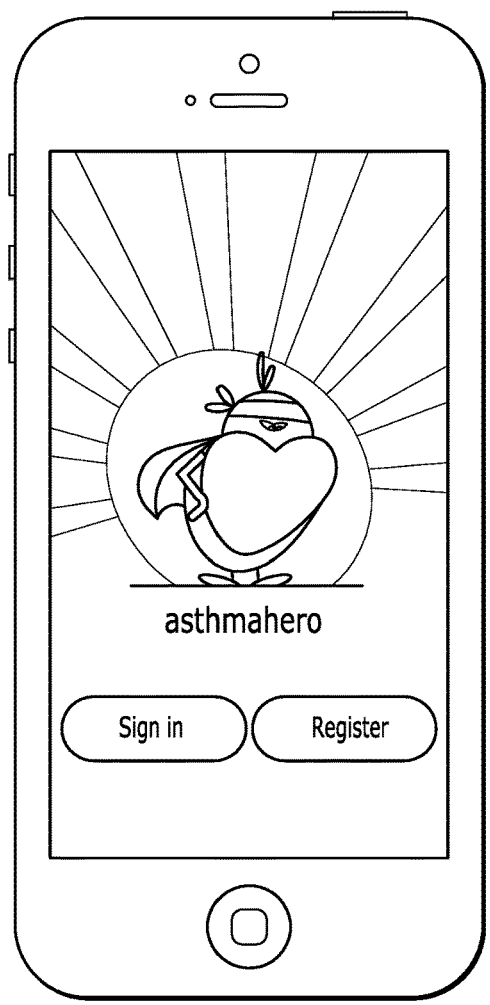
FIGS. 7-9 show screens presented to the user by the adherence monitoring application during welcome and setup.
Figure 8:
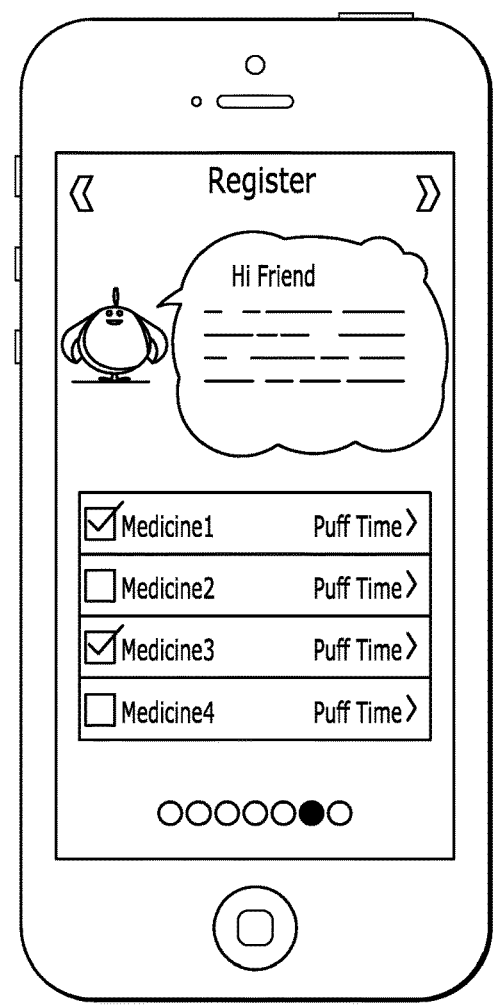
Figure 9:
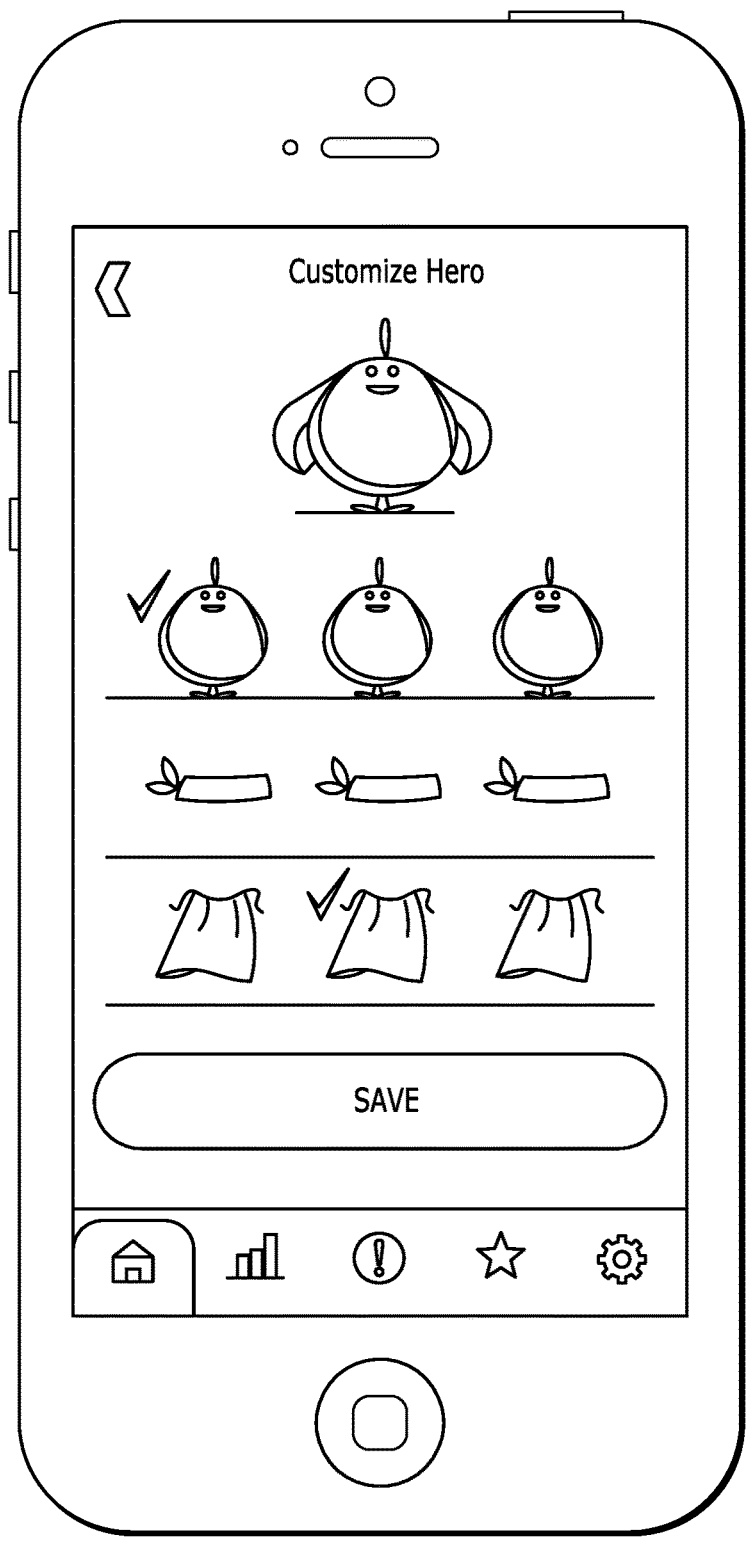

FIGS. 7-9 are examples of screens presented during initial setup of the application.

Figure 10:
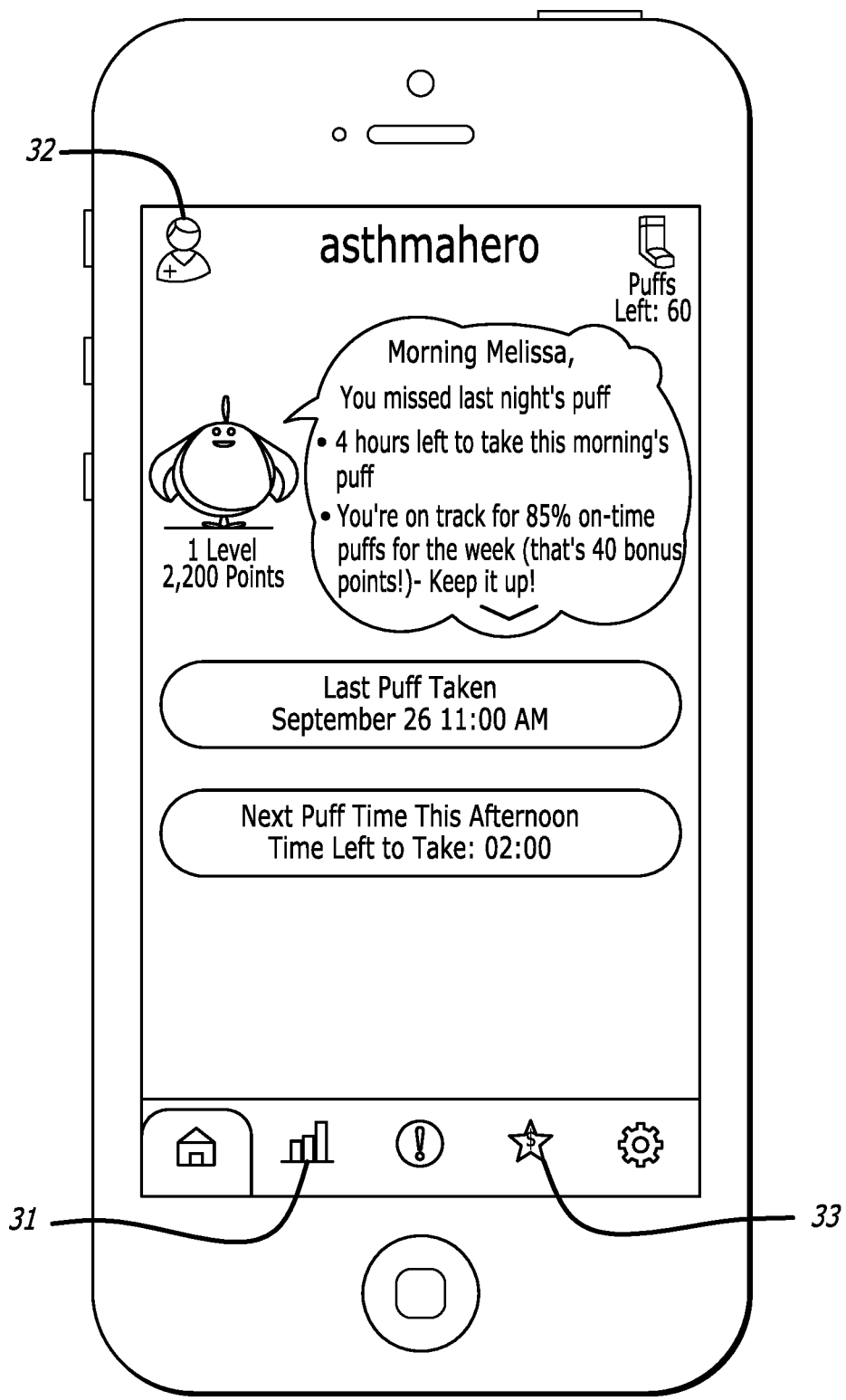
FIGS. 10-14 illustrate screens presented to the user by the adherence monitoring application during subsequent operation of the adherence monitoring system.

FIG. 10 shows an example of a home screen when the application is thereafter loaded, with notations of missed, taken and scheduled puffs, and a statement of the overall compliance record and achievement of incentives. The home screen of FIG. 10, like most screens, displays the avatar "Hero", and messaging from the avatar based on criteria and formulas coded into the application and server. The Hero avatar has a status level (depending upon HeroPoints achieved), and customized features (e.g., hat, shape, color) depending on user preference (and possibly hero level, e.g., if some features are only unlocked at a certain HeroLevel) set in the setup process reflected in FIGS. 7-9; and displays HeroPoints and/or other awards, e.g., gold coins or other virtual currency that can be used to purchased rewards in the Reward Zone.

The bottom of the home screen has links to Settings, RewardZone, Emergency Call, and AdheroMeter.

Pressing the Emergency Call icon can initiate an emergency communication, which can be a telephone call, SMS or other text message, email, etc., to a physician or other healthcare professional, a caregiver or other emergency contact person.

The top left of the home screen presents an icon for a Doctor's Appointment Page. The home screen also displays (in the upper right corner) an inhaler icon, which provides information on how many doses are left in current inhaler cartridge. A "!" (not shown) near a faded inhaler icon can indicate that no tracking module is paired with the application. A triple ")))" near the inhaler icon can indicate that a tracking module is synced. Clicking the inhaler icon can lead to an order refill page.

The home screen also displays the last time medication was taken, as well as the time left to take medication within dosage instructions provided by prescription (as entered by the user or physician). For example, "twice a day" controller medications are separated into two "Puff Time Intervals," (a) 1 am-1 pm and (b) 1:01 pm-1 am. During the afternoon, the Home screen will display the time remaining until 1 am.

Figure 11:
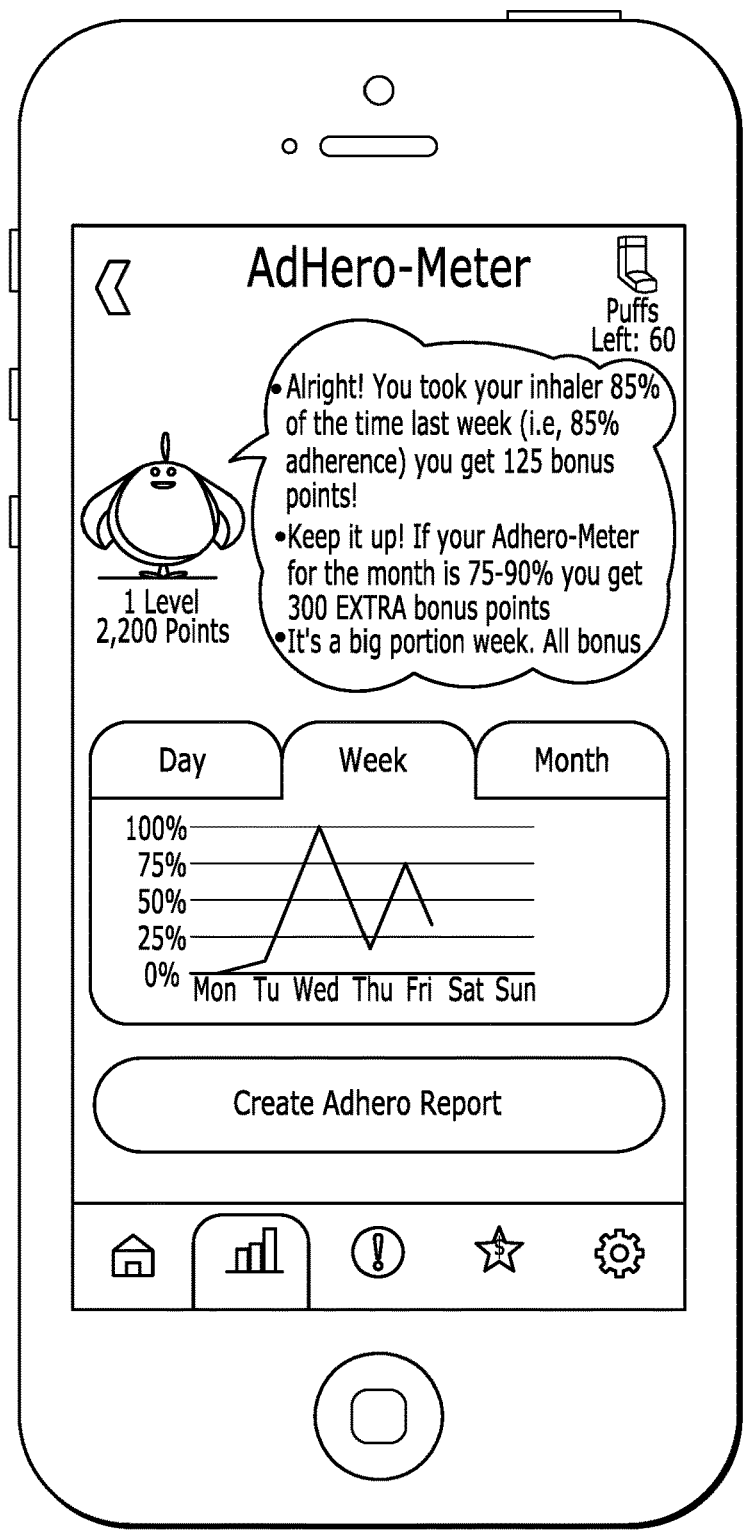

FIG. 11 shows an example of a graphical presentation of the weekly compliance report available to the user on pressing the report (AdheroMeter) icon 31. This screen displays the Hero avatar, along with appropriate messaging from the avatar based on formulas coded into the application. The Hero avatar has status level depending upon HeroPoints achieved (which are also displayed), and customized features depending on user preference (hat, cape, color). This screen also contains lines to all other screens, e.g., the bottom of the screen has links to Settings, RewardZone, Emergency Call and Home screens, with the center of the screen presenting a an icon to a Create AdHero Report page, and the upper right of the screen displaying an inhaler icon, which provides information on how many doses are left in current inhaler cartridge. As before, a "!" near a faded inhaler icon can indicate that no tracking module is paired with the application, whereas a triple ")))" near the inhaler icon can indicate that a tracking module is synced, and clicking on the inhaler icon leads to an Order-Refill page.

The screen displays a graphical representation of adherence rate (as a percentage) on a daily, weekly, and monthly basis, and also informs the user of rewards (HeroPoints) earned for past) per an award schedule disclosed in the settings process. Finally, at the upper left of the screen is a "Back" arrow for returning to the previous screen.

Figure 12:
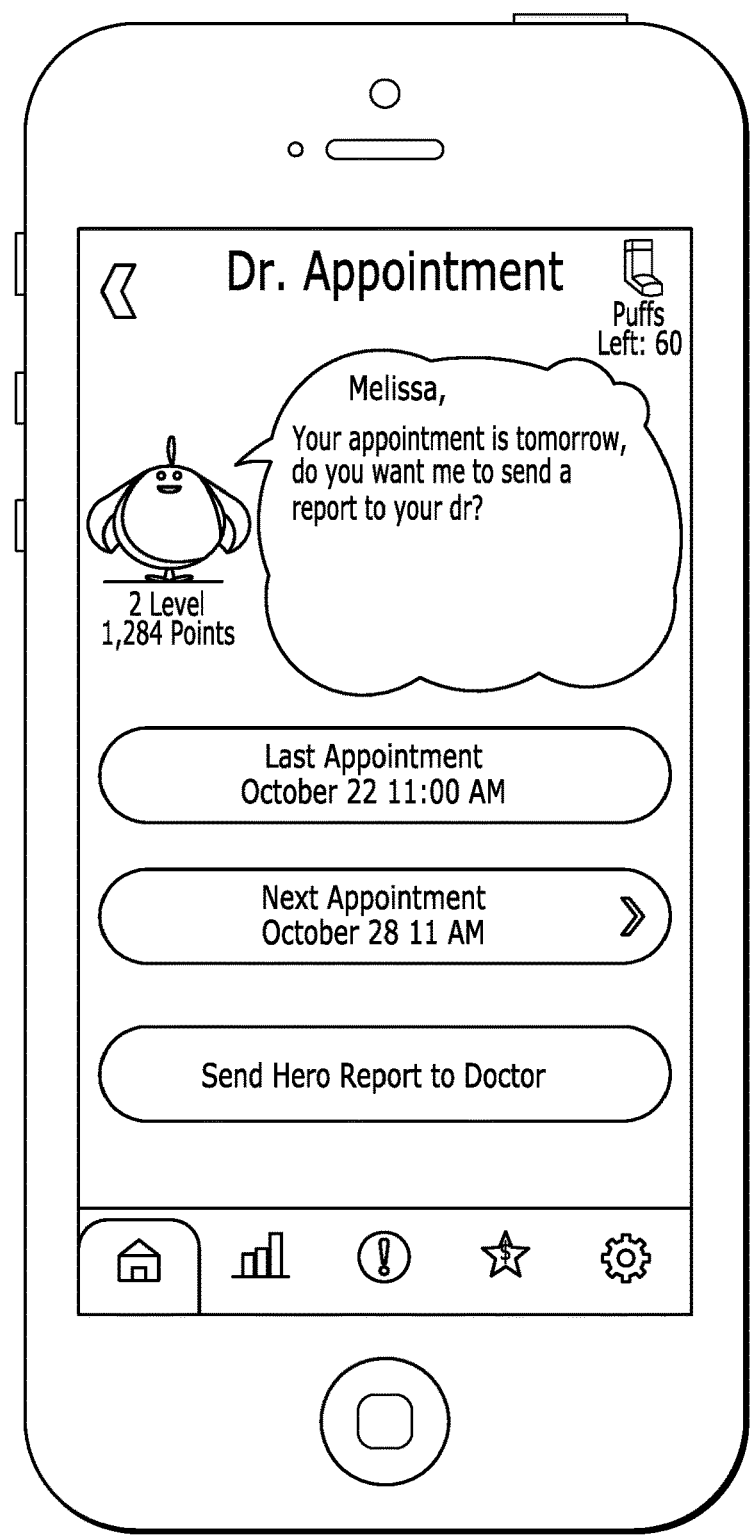

FIG. 12 shows an example of doctor's appointment reminder that can be brought up by selecting the Dr. Appointment icon 32 at the upper left of the screen in FIG. 10. This screen displays the Hero avatar, along with appropriate messaging from the avatar. The Hero avatar has status level depending upon HeroPoints achieved (which are also displayed), and customized features depending on user preference (hat, cape, color). This screen also contains lines to all other Hero screens, e.g., the bottom of the screen has links to Settings, RewardZone, Emergency Call, Home and AdheroMeter screens, with the center of the screen presenting an icon to send a report to the doctor. This may trigger the server 50 to send a 1-page Hero report to a doctor's email address if such has been entered by the user in "settings," or manually entered on this screen, and/or to a doctor's electronic medical record system, when synced with the server or phone.

The upper right of the screen displays an inhaler icon, which provides information on how many doses are left in current inhaler cartridge. Optionally, this icon is a link so that touching this icon takes the user to another screen having prescription information including an icon which can be selected to electronically send a prescription refill request to a pharmacy. This could be implemented, e.g., by having the smartphone send a prescription request to the server 50 and for the server to then send a prescription refill request (an "e-prescription") to the pharmacy by facsimile or other electronic transmission. Add automaticAs before, a "!" near a faded inhaler icon can indicate that no tracking module is paired with the application, whereas a triple ")))" near the inhaler icon can indicate that a tracking module is synced, and clicking on the inhaler icon leads to an Order-Refill page. This screen also displays the last appointment date (if known), as well as the next appointment date (and provides the ability to set that date).

Figure 13:
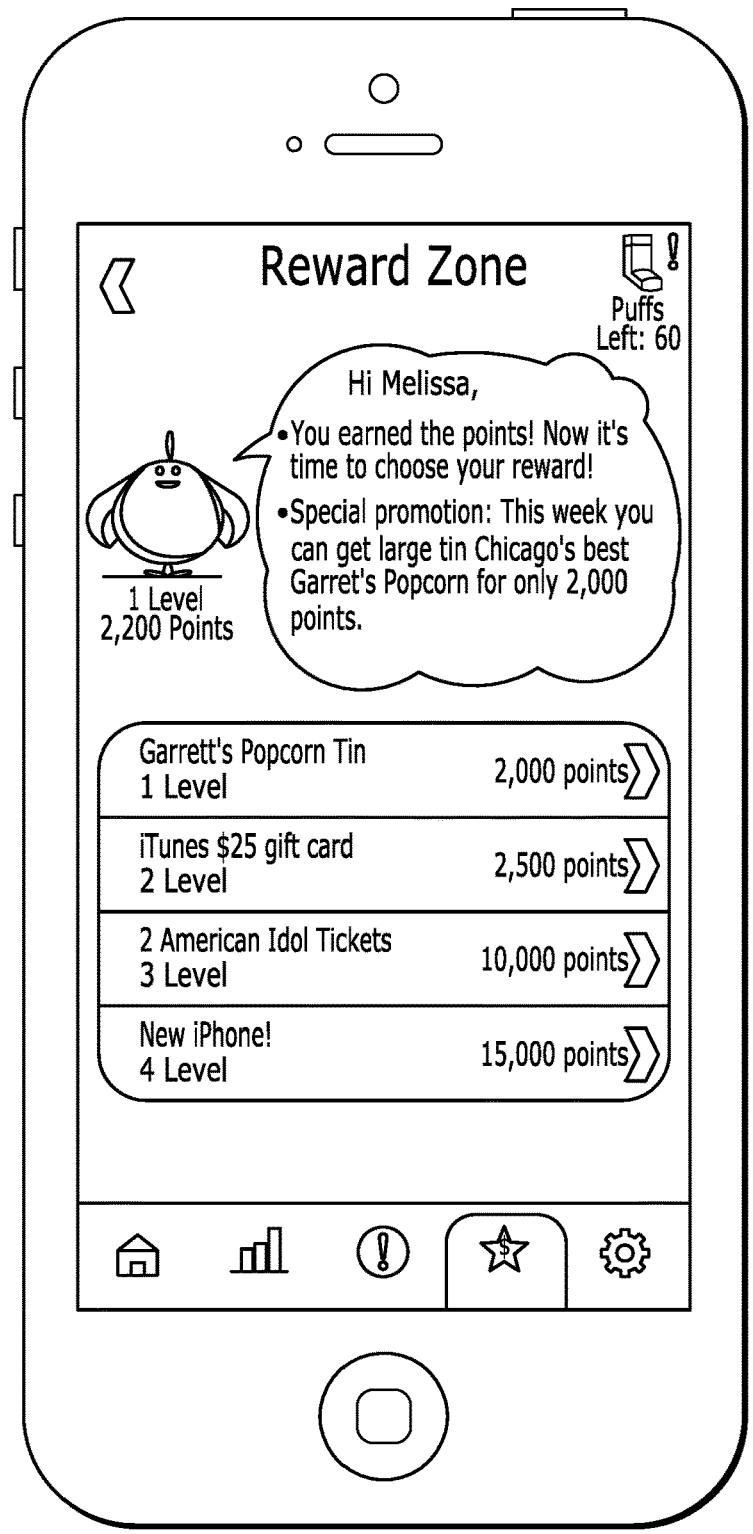

FIG. 13 shows an example of a reward zone screen that can be displayed to the user by pressing the reward zone icon 33. This screen displays the Hero avatar, along with appropriate messaging from the avatar. As in other screens, the Hero avatar has status level depending upon HeroPoints achieved (which are also displayed), and customized features depending on user preference (hat, cape, color). This screen also contains lines to all other Hero screens, e.g., the bottom of the screen has links to Settings, RewardZone, Emergency Call, AdheroMeter and Home screens, with the center of the screen presenting icons for redeeming earned points. Certain rewards can be reserved exclusively for Level 2 and Level 3 users. Each reward shows the cost in virtual currency (gold coins) or points or other way. Rewards that the user has sufficient virtual currency to purchase are displayed in a manner distinct from unavailable rewards to signify the user can purchase them. A user selects which reward they would like to purchase, virtual currency is deducted and an order is processed to send the reward to the patient.

The upper right of the screen displays an inhaler icon, which provides information on how many doses are left in current inhaler cartridge. As before, a "!" near a faded inhaler icon can indicate that no tracking module is paired with the application, whereas a triple ")))" near the inhaler icon can indicate that a tracking module is synced, and clicking on the inhaler icon leads to an Order-Refill page. This screen also displays a "Back" arrow in its upper left, for returning to the previous screen.

Figure 14:
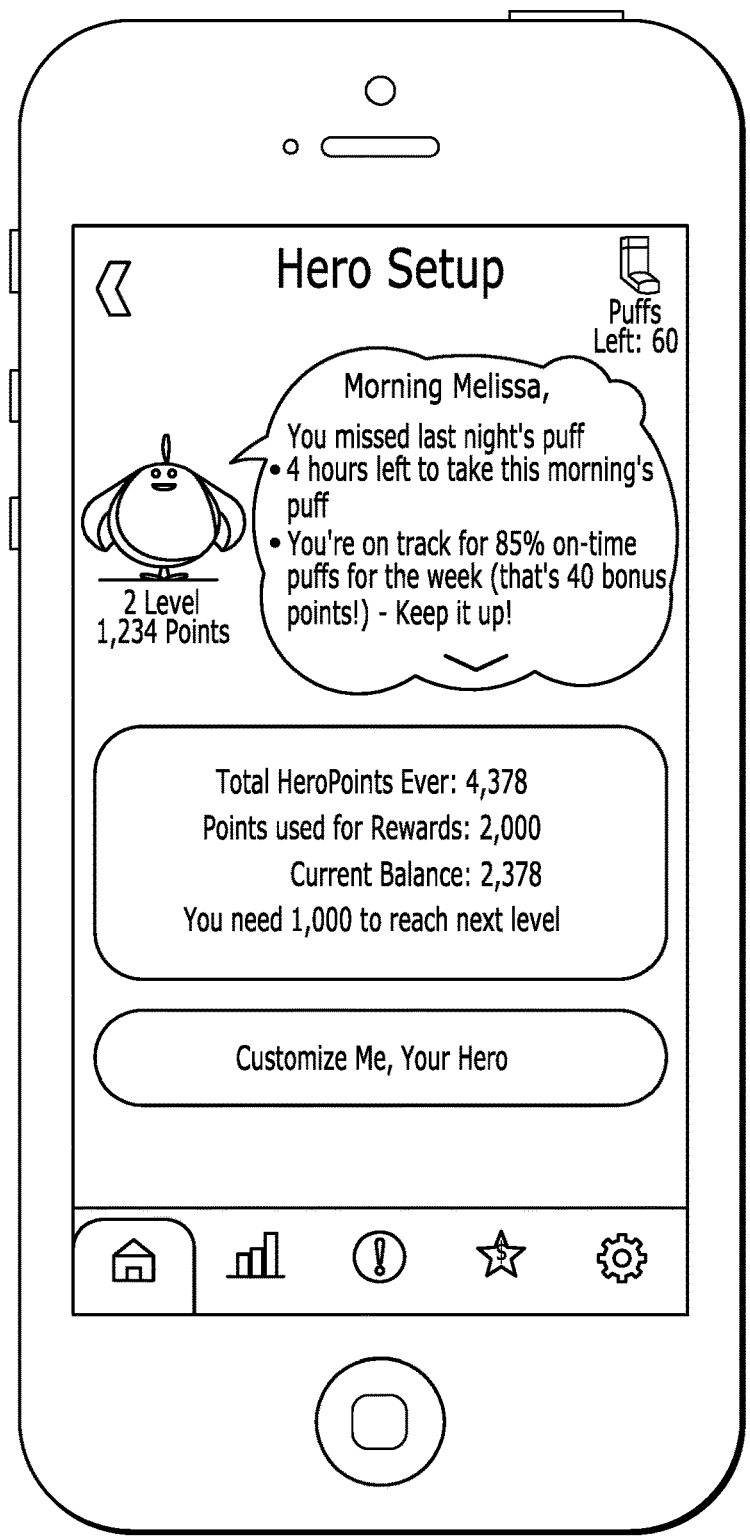

FIG. 14 shows an example of a Hero Setup screen reached by, e.g., touching the Hero icon and then selecting "Customize." This screen displays the Hero avatar, along with appropriate messaging from the avatar. The Hero avatar has status level depending upon HeroPoints achieved (which are also displayed), and customized features depending on user preference (hat, cape, color). This screen also contains lines to all other Hero screens, e.g., the bottom of the screen has links to Settings, RewardZone, Emergency Call, Home and AdheroMeter screens, with the center of the screen presenting a more detailed report of the Hero level status and goal, and also including a Customize icon which will bring up the screen shown in FIG. 9.

The upper right of the screen displays an inhaler icon, which provides information on how many doses are left in current inhaler cartridge. As before, a "!" near a faded inhaler icon can indicate that no tracking module is paired with the application, whereas a triple ")))" near the inhaler icon can indicate that a tracking module is synced, and clicking on the inhaler icon leads to an Order-Refill page.

The above screens can be modified or additional screens added to show an alert to the patient of a potential adverse event or other complication, an alert regarding a change in the treatment regimen, an alert to the patient to contact the physician, etc.

While the invention has thus far been described primarily in the context of an inhaler, it can be used to alternatively or additionally track spirometer usage, as briefly indicated above with regard to FIG. 1. A spirometer is used to assess lung function, with the user blowing into the spirometer which then measures the strength and volume of an exhalation and/or inhalation. These measurements are transmitted to a local station 30 and/or to remote server 50. It is also possible for a tracking module 10 to be paired with a spirometer so that the tracking module could store respiratory data reflecting spirometer measurements. This could be done with a tracking module dedicated to the spirometer, or separate tracking modules for spirometer and inhaler, or the spirometer could have the elements of a tracking module (e.g., activation sensor, internal memory, wireless communication component) incorporated within the spirometer. The interactive user interface presented by the local station could have a separate interface dedicated to spirometer usage, or if inhaler usage data is collected in addition to spirometer measurements, a single interface could address both inhaler and spirometer usage.

In either case, the local station (e.g., smartphone) could display animations similar to those described above in the context of inhaler usage, and/or other images that correlate to the users inspiration or expiration. For example, an image of a birthday cake with candles where the candles flicker and are extinguished as a user blows into the spirometer.

By tracking these lung function measurements over time, trends can be identified. Response to different inhaler treatment regimens could be seen, deterioration of lung function suggesting imminent respiratory event could be spotted, and predictive modeling could be used with all available data to predict potential future events/issues more reliably and provide appropriate messages to the patient and/or healthcare support to prevent such events. By way of example, the system could generate communications relating to a potential exacerbation, potential complication, potential acute event, effectiveness of current usage plan and/or potential change to the usage plan. The patient could, e.g., in a Settings menu, designate different persons to receive communications, e.g., a caregiver designated to receive communications regarding compliance level, potential acute events, etc., and a physician or medical practice receiving communications relating to potential acute events and also communications relating to the effectiveness of a current usage plan or potential change to that plan. For example, a communication to the healthcare professional relating to the current or potential usage plan could be data on usage and lung function, or could also include analysis of that data. A further option would be designating an insurance provider to receive communications regarding a prescription refill.

The smartphone app could also instruct the user on proper use of the spirometer, and could provide incentives for proper usage if desired. The spirometer could also have it's own internal memory, so it could be used while not in proximity to a local station or to a tracking module, and data could be synced at a later time either to a tracking module or directly to a local station.

We claim:

1. A system for monitoring and facilitating use of a respiratory device by a patient, wherein the respiratory device comprises an inhaler having a body with an opening at the top into which is positioned a canister of respiratory medication, and a mouthpiece, the body and canister having complementary interactive configurations such that depressing the canister into the body causes the canister to deliver a treatment dose of the respiratory medication through the mouthpiece to be administered to the patient, the patient having a usage plan of the inhaler, the system comprising:
  a tracking module comprising a flexible shell configured to be mounted around and in contact with the body of the inhaler, the flexible shell having embedded therein a tracking module memory, a tracking module battery, and a tracking module communication component, the flexible shell also comprising an inhaler activation sensor connected with the shell memory, the activation sensor comprising a pressure-activated switch located in a cap outside the shell connected to the shell with a flexible cable, the cap being located in contact with the canister at the top of the inhaler body such that a user must press the pressure-activated switch when depressing the inhaler canister for activation of the inhaler thereby causing the pressure-activated switch to provide an inhaler activation signal, and to store an inhaler activation signal in the tracking module memory each time the inhaler is activated in this way, the tracking module memory storing inhaler activation data relating to each detected activation of the inhaler as inhaler data, the communication component configured to wirelessly transmit the stored inhaler data; and
  a processor located at a local station removed from the inhaler and tracking module mounted thereto, the processor storing the patient's inhaler usage plan and configured to communicate with the communication component of the tracking module, receive the stored inhaler data from the tracking module memory, compare it to the inhaler usage plan, and interact with the patient by providing a statement of compliance of the patient with the usage plan.

2. The system according to claim 1, wherein the local station further comprises a display connected with the processor, wherein the processor determines from the stored inhaler data received from the tracking module memory the number of doses remaining in the canister of the inhaler and controls the display to visually display an indication of the number of doses remaining in the inhaler.

3. The system according to claim 2, wherein the processor is configured to determine from the received stored inhaler data from the tracking module memory the number of doses remaining in the canister of the inhaler, and is further configured to respond to that information to send a prescription refill request to a medication supplier.

4. A system in which the same patient is using a second respiratory device comprising a spirometer, the spirometer providing lung function data of the patient, the system according to claim 1, wherein the processor also receives the lung function data from the spirometer and correlates the lung function data with the inhaler data.

5. The system according to claim 4, wherein the processor is also configured to control the display to visually display lung function over time.

6. A system in which the same patient is also using a second respiratory device comprising a rescue inhaler, the rescue inhaler also having a body with an opening at the top into which is positioned a canister of rescue respiratory medication, and a mouthpiece, the body and canister having complementary interactive configurations such that depressing the canister into the body causes the canister to deliver a treatment dose of the rescue respiratory medication through the mouthpiece to be administered to the patient, the system according to claim 4, wherein one respiratory device is a controller medication inhaler and a second respiratory device is a rescue medication inhaler, and a third device is the spirometer;
  the rescue inhaler providing a rescue inhaler activation signal each time the rescue inhaler is activated and wirelessly communicating each rescue inhaler activation signal;
  wherein the processor is further configured to communicate with the spirometer, the controller inhaler, and the rescue inhaler to receive the lung function data, the rescue inhaler activation data, and the controller inhaler data, to correlate all data and to perform predictive analytics on lung function data, controller medication inhaler data, and rescue inhaler medication data, to predict potential future events and issues and transmit messages relevant to the predictions.

7. The system according to claim 6, wherein the predictions relate to at least one of potential exacerbation, potential complication, potential acute event, effectiveness of current usage plan, and potential change to said usage plan.

8. A system in which the same patient is using a second respiratory device comprising a rescue inhaler, the rescue inhaler also having a body with an opening at the top into which is positioned a canister of rescue respiratory medication, and a mouthpiece, the body and canister having complementary interactive configurations such that depressing the canister into the body causes the canister to deliver a treatment dose of the rescue respiratory medication through the mouthpiece to be administered to the patient, the system according to claim 1, wherein one respiratory device is a controller medication inhaler and a second respiratory device is a rescue medication inhaler;

the rescue inhaler providing a rescue inhaler activation signal each time the rescue inhaler is activated and wirelessly communicating each rescue inhaler activation signal;

wherein the processor is further configured to communicate with the rescue inhaler to receive the rescue inhaler activation signals and to correlate the rescue inhaler signals with the controller medication inhaler activation signals.

9. The system according to claim 1, wherein the local station further comprises a display connected with the processor, wherein the processor is configured to visually provide the statement of compliance with the usage plan on the display.

10. The system according to claim 9, wherein the processor is also configured to determine from the stored usage plan the next scheduled use of the inhaler and control the display to visually display the next scheduled use.

11. The system according to claim 9, wherein the processor of the local station is also configured to display a link for initiating an emergency communication.

12. The system according to claim 9, wherein the processor of the local station is also configured to display a link for a prescription refill, and is further configured to generate an e-prescription directly to a pharmacy.

13. The system according to claim 1, wherein the flexible shell is formed of a stretchable material whereby when it is secured to the outside of an inhaler, the flexible shell stretches to conform to a shape of the inhaler and its tendency to contract secures it to the inhaler, and its stretchable material permits it to be secured to inhalers of different sizes.

14. The system according to claim 1, further comprising a remote server in communication with the local station, wherein the remote server is configured to store a patient's inhaler usage plan, receive the inhaler data from the processor of the local station, determine the patient's compliance with the usage plan, and make the determination available to those having authorization to access the server.

15. The system according to claim 14, wherein the remote server is also configured to generate communications, including alerts, regarding the patient's compliance with the usage plan to a third party selected from the group comprising a healthcare professional, a family member, an insurance carrier, and a caregiver.

16. The system according to claim 14, wherein the remote server is also configured to generate communications that include lung function data and medication usage plan compliance data to send to an Electronic Medical Records system of a physician.

17. The system according to claim 1, wherein said local station comprises a smartphone.

18. The system according to claim 1, wherein at least one of the tracking module and the local station is configured to issue an alert to the patient if the respiratory device is not used according to the usage plan.

19. The system according to claim 1, wherein said tracking module is configured to respond to detected pressure on the pressure-activated switch of the flexible shell during depressing of said canister by:

awakening from a standby mode;

storing inhaler activation signals in the tracking module memory;

searching for proximity to the local station, and transmitting stored inhaler activation data to the local station when the local station is found; and returning to standby mode after transmission of the stored inhaler activation data to the local station.

20. The system according to claim 1 wherein the processor of the local station is further configured to provide reminders to the patient according to the usage plan, the frequency of the reminders being dependent on at least one of patient behavior and patient preference.

21. The system according to claim 20 wherein the processor is further configured to decrease the frequency of the reminders in response to increased patient compliance with the usage plan.

22. The system according to claim 1, wherein the tracking module is configured to:

operate in an off/standby mode to conserve life of the battery;

automatically awaken to store a date/time stamp when the pressure-activated switch detects pressure on the canister when depressing the canister;

thereafter attempt to connect with the local station processor to transfer the date/time stamp data; but if unsuccessful in connecting with the processor, will continue trying at intervals to connect with the processor until successful;

whereby the local station processor need not be in proximity when an inhaler dose is taken.

23. A system for monitoring and facilitating use of a respiratory device by a patient, wherein the respiratory device comprises an inhaler having a body with an opening at the top into which is positioned a canister of respiratory medication, and a mouthpiece, the body and canister having complementary interactive configurations such that depressing the canister into the body causes the canister to deliver a treatment dose of the respiratory medication through the mouthpiece to be administered to the patient, the patient having a usage plan of the inhaler, the system comprising:

a tracking module comprising a flexible shell configured to be mounted around and in contact with the body of the inhaler, the flexible shell having embedded therein a tracking module memory, a tracking module battery, and a tracking module communication component, the flexible shell also comprising an inhaler activation sensor connected with the shell memory, the activation sensor comprising a pressure-activated switch located in a cap outside the shell connected with the shell, the cap being located in contact with the canister at the top of the inhaler body such that a user must press the pressure-activated switch when depressing the canister for activation of the inhaler thereby causing the pressure-activated switch to provide an inhaler activation signal, and to store the inhaler activation signal in the tracking module memory each time the inhaler is activated in this way, the tracking module memory storing activation data relating to each detected activation of the inhaler as inhaler data, the communication component configured to wirelessly transmit the stored inhaler data;

a processor located at a handheld local station removed from the inhaler and tracking module mounted thereto, the processor storing the patient's inhaler usage plan and configured to communicate with the communication component of the tracking module, receive the stored inhaler data from the tracking module memory, compare it to the inhaler usage plan, and interact with the patient by providing a statement of compliance of the patient with the usage plan;

a display connected with the processor, wherein the processor determines from the stored inhaler data received from the tracking module memory the number of doses remaining in the canister of the inhaler and controls the display to visually display an indication of the number of doses remaining in the inhaler, the processor also being configured to control the display to display the statement of compliance with the usage plan on the display; and a remote server in communication with the local station, wherein the remote server is configured to store a patient's inhaler usage plan, receive the inhaler data from the processor of the local station, determine the patient's compliance with the usage plan, and make the compliance determination available to those having authorization to access the server;

wherein at least one of the tracking module, the local station, and the remote server is configured to issue an alert to the patient if the inhaler is not used according to the usage plan.

24. The system for monitoring and facilitating use of a respiratory device by a patient in which the same patient is using a second respiratory device comprising a spirometer, the spirometer providing lung function data of the patient, the system, according to claim 23, wherein the processor also receives the lung function data from the spirometer and correlates the lung function data with the inhaler data.

25. The system for monitoring and facilitating use of a respiratory device by a patient according to claim 23, wherein the processor is also configured to control the display to visually display lung function over time.

26. A system in which the same patient is using a second respiratory device comprising a rescue inhaler, the rescue inhaler also having a body with an opening at the top into which is positioned a canister of rescue respiratory medication, and a mouthpiece, the body and canister having complementary interactive designs such that depressing the canister into the body causes the canister to provide a treatment dose of the rescue respiratory medication through the mouthpiece to be administered to the patient, the system according to claim 25, wherein one respiratory device is a controller medication inhaler and a second respiratory device is a rescue medication inhaler, the rescue inhaler providing a rescue inhaler activation signal each time the rescue inhaler is activated and wirelessly communicating each rescue inhaler activation signal, wherein the processor is further configured to communicate with the rescue inhaler to receive the rescue inhaler activation signals and to correlate the rescue inhaler signals with the controller medication inhaler activation signals.

27. A system for monitoring and facilitating use of respiratory devices by a patient, wherein the respiratory devices comprise a controller inhaler and a rescue inhaler, each of which has a body with an opening at the top into which is positioned a canister of respiratory medication, and a mouthpiece, the body and canister having a complementary interactive configuration such that depressing the canister into the body causes the canister to provide a treatment dose of the respiratory medication through the mouthpiece to be administered to the patient, the patient having a usage plan for the controller inhaler, the system comprising:

a separate tracking module attached to each of the controller and rescue inhalers, each tracking module comprising a flexible shell configured to be secured around and in contact with the body of the inhaler, the flexible shell having embedded therein a tracking module memory, a tracking module battery, and a tracking module communication component, the flexible shell also comprising an inhaler activation sensor connected with the shell memory, the activation sensor comprising a pressure-activated switch located in a cap outside the shell connected to the shell with a flexible cable, the cap being located in contact with the canister at the top of the inhaler body such that a user must press the pressure-activated switch when depressing the inhaler canister for activation of the inhaler thereby causing the pressure-activated switch to provide an inhaler activation signal, and to store an inhaler activation signal in the tracking module memory each time the inhaler is activated in this way, the tracking module memory storing inhaler activation data relating to each detected activation of the inhaler as inhaler data, the communication component configured to wirelessly transmit the stored inhaler data;

wherein each of the tracking modules attached to the controller and the rescue inhaler is configured to:

operate in an off/standby mode to conserve life of the battery;

automatically awaken to store a date/time stamp when inhaler is used;

thereafter attempt to connect with the local station processor to transfer the date/time stamp data; but if unsuccessful in connecting with the processor, will continue trying at intervals to connect with the processor until successful;

whereby the local station processor need not be in proximity when an inhaler dose is taken;

a spirometer configured to sense the lung function of a patient and provide lung function data representative thereof;

a processor located at a handheld local station removed from the inhalers and tracking modules mounted thereto, the processor storing the patient's controller inhaler usage plan and configured to communicate with the communication component of each of the tracking modules, receive the stored inhaler data from each tracking module memory, compare it to the usage plan, and interact with the patient by providing a statement of compliance of the patient with the inhaler usage plan, the processor also configured to receive the lung function data from the spirometer and correlate the lung function data with the inhaler data;

a display connected with the processor, wherein the processor determines from the stored data of the inhalers received from the tracking modules' memories the number of doses remaining in the canister of each of the inhalers and controls the display to visually display an indication of the number of doses remaining in the inhalers, the processor also configured to control the display to visually display lung function over time; and a remote server connected with the local station, wherein the remote server is configured to receive a patient's inhaler usage plan, receive the inhaler data from the processor of the local station, determine the patient's compliance with the usage plan, and make the determination available to those having authorization to access the server;

wherein at least one of the tracking modules, the local station, and the server is configured to issue an alert to the patient if the controller respiratory device is not used according to the usage plan.

\* \* \* \* \*